United States Patent
Hu et al.

(10) Patent No.: US 11,564,565 B2
(45) Date of Patent: Jan. 31, 2023

(54) CHIP-SCALE OPTICAL COHERENCE TOMOGRAPHY ENGINE

(71) Applicant: Massachusetts Institute of Technology, Cambridge, MA (US)

(72) Inventors: Juejun Hu, Newton, MA (US); Tian Gu, Fairfax, VA (US); Derek Kita, Cambridge, MA (US); Carlos Andres Rios Ocampo, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/165,001

(22) Filed: Feb. 2, 2021

(65) Prior Publication Data

US 2021/0307603 A1 Oct. 7, 2021

Related U.S. Application Data

(60) Provisional application No. 63/003,956, filed on Apr. 2, 2020.

(51) Int. Cl.
*G01B 11/02* (2006.01)
*A61B 3/10* (2006.01)
(Continued)

(52) U.S. Cl.
CPC .......... *A61B 3/102* (2013.01); *G01B 9/02091* (2013.01); *G02B 27/106* (2013.01)

(58) Field of Classification Search
CPC ............ G01B 9/02091; G01B 9/02027; G01B 9/02044; A61B 3/102; G02B 27/106; G01J 3/0256; G01J 3/453
See application file for complete search history.

(56) References Cited

U.S. PATENT DOCUMENTS

| 5,222,162 A | 6/1993 | Yap et al. |
| 5,233,673 A | 8/1993 | Vali et al. |

(Continued)

OTHER PUBLICATIONS

Agrawal et al., "Methods to assess sensitivity of optical coherence tomography systems." Biomedical optics express 8.2 (2017): 902-917.

(Continued)

*Primary Examiner* — Tarifur R Chowdhury
*Assistant Examiner* — Jonathon Cook
(74) *Attorney, Agent, or Firm* — Smith Baluch LLP

(57) ABSTRACT

An optical coherence tomography (OCT) engine includes a digital Fourier-Transform (dFT) spectrometer, a tunable delay line, and a high-speed optical phased array (OPA) scanner integrated onto a single chip. The broadband dFT spectrometer offers superior signal-to-noise ratio (SNR) and fine axial resolution; the tunable delay line ensures large imaging depth by circumventing sensitivity roll-off; and the OPA can scan the beams at GHz rates without moving parts. Unlike conventional spectrometers, the dFT spectrometer employs an optical switch network to retrieve spectral information in an exponentially scaling fashion—its performance doubles with every new optical switch added to the network. Moreover, it also benefits from the Fellgett's advantage, which provide a significant SNR edge over conventional spectrometers. The tunable delay line balances the path length difference between the reference and sample arms, avoiding any need to sample high-frequency spectral fringes.

22 Claims, 8 Drawing Sheets

(51) Int. Cl.
    *G02B 27/10*       (2006.01)
    *G01B 9/02091*     (2022.01)

(56) References Cited

U.S. PATENT DOCUMENTS

| | | | |
|---|---|---|---|
| 8,988,754 | B2 | 3/2015 | Sun et al. |
| 2004/0073101 | A1 | 4/2004 | Chance |
| 2005/0018201 | A1 | 1/2005 | De Boer et al. |
| 2006/0103850 | A1 | 5/2006 | Alphonse et al. |
| 2014/0085632 | A1 | 3/2014 | Preston et al. |
| 2014/0115022 | A1 | 4/2014 | Yasuno et al. |
| 2014/0125983 | A1 | 5/2014 | Nitkowski et al. |
| 2014/0299771 | A1 | 10/2014 | Rahman |
| 2014/0376001 | A1* | 12/2014 | Swanson ............ G01N 21/17 356/479 |
| 2017/0227399 | A1* | 8/2017 | Hu ..................... G02F 1/3136 |
| 2017/0268987 | A1 | 9/2017 | Swanson |
| 2019/0000820 | A1 | 1/2019 | Blight et al. |
| 2019/0029512 | A1 | 1/2019 | Pulaski et al. |
| 2019/0049300 | A1* | 2/2019 | Gu ....................... G01J 3/0259 |
| 2019/0219888 | A1 | 7/2019 | Sun et al. |
| 2019/0269320 | A1 | 9/2019 | Holland et al. |
| 2021/0025690 | A1* | 1/2021 | Tearney ............ G01B 9/02087 |

OTHER PUBLICATIONS

Akca et al., "Miniature spectrometer and beam splitter for an optical coherence tomography on a silicon chip." Optics Express 21.14 (2013): 16648-16656.

AQ6360 Telecom Production Optical Spectrum Analyzer 1200-1650 nm. Test & Measurement Corporation. Accessed a https://tmi.yokogawa.com/us/solutions/products/optical-measuring-instruments/optical-spectrum-analyzer/aq6360-optical-spectrum-analyzer/ on Apr. 23, 2020. 5 pages.

Chang et al., "Chip based common-path optical coherence tomography system with an on-chip microlens and multi-reference suppression algorithm." Optics Express 24.12 (2016): 12635-12650.

Choma et al., "Sensitivity advantage of swept source and Fourier domain optical coherence tomography." Optics Express 11.18 (2003): 2183-2189.

Drexler et al., "Optical coherence tomography today: speed, contrast, and multimodality." Journal of Biomedical Optics 19.7 (2014): 071412. 35 pages.

Gatkine et al., "Arrayed waveguide grating spectrometers for astronomical applications: new results." Optics Express 25.15 (2017): 17918-17935.

Geuzebroek et al., "Ultra-wide band (400-1700nm) integrated spectrometer based on arrayed waveguide gratings for spectral tissue sensing." 2017 IEEE 14th International Conference on Group IV Photonics (GFP). IEEE, 2017. 2 pages.

Hagen-Eggert et al., "Analysis of the signal fall-off in spectral domain optical coherence tomography systems." Optical Coherence Tomography and Coherence Domain Optical Methods in Biomedicine XVI. Vol. 8213. International Society for Optics and Photonics, 2012. 7 pages.

Huang et al., "Optical coherence tomography." Science 254.5035 (1991): 1178-1181.

Israelsen et al., "Real-time high-resolution mid-infrared optical coherence tomography." Light: Science & Applications 8.1 (2019): 1-13.

Klein et al., "High-speed OCT light sources and systems." Biomedical Optics Express 8.2 (2017): 828-859.

Kodach et al., "Quantitative comparison of the OCT imaging depth at 1300 nm and 1600 nm." Biomedical Optics Express 1.1 (2010): 176-185.

Leitgeb et al., "Performance of fourier domain vs. time domain optical coherence tomography." Optics Express 11.8 (2003): 889-894.

Lin et al., "Mid-infared integrated photonics on silicon: a perspective." Nanophotonics 7.2 (2017): 393-420.

Margallo-Balbás et al., "Miniature 10 kHz thermo-optic delay line in silicon." Optics Letters 35.23 (2010): 4027-4029.

Maria et al., "Q-switch-pumped supercontinuum for ultra-high resolution optical coherence tomography." Optics Letters 42.22 (2017): 4744-4747.

Nitkowski et al., "On-chip spectrometer for low-cost optical coherence tomography." Optical Coherence Tomography and Coherence Domain Optical Methods in Biomedicine XVIII. Vol. 8934. International Society for Optics and Photonics, 2014. 9 pages.

OCT Light Sources☐: Extended Broadband SLD Source. Alahram. Accessed at http://www.aitc-group.com/alahram2/index.php/products/imaging/microscopy-systems/oct-imaging/oct-components/oct-light-sources/extended-broadband-sld-source-detail on Apr. 23, 2020. 4 pages.

OCT Selection Guide. ThorLabs. Accessed at https://www.thorlabs.com/newgrouppage9.cfm?objectgroup_id=5702 on Apr. 23, 2020. 3 pages.

Ruis et al., "Decreasing the size of a spectral domain optical coherence tomography system with cascaded arrayed waveguide gratings in a photonic integrated circuit." IEEE Journal of Selected Topics in Quantum Electronics 25.1 (2018): 1-9.

Schneider et al., "Optical coherence tomography system mass-producible on a silicon photonic chip." Optics Express 24.2 (2016): 1573-1586.

Telesto Series SD-OCT Systems. Thorlabs. Accessed at https://www.thorlabs.com/newgrouppage9.cfm?objectgroup_id=12569&pn=TEL320C1 on Apr. 23, 2020. 6 pages.

Tutorial: InGaAs vs. Ge IR Detectors. Newport. Accessed at https://www.newport.com/n/ingaas-vs-ge-ir-detectors on Apr. 23, 2020. 2 pages.

Van Leeuwen et al., "On-chip Mach-Zehnder interferometer for OCT systems." Advanced Optical Technologies 7.1-2 (2018): 103-106.

Wang et al., "Phase error corrected 4-bit true time delay module using a cascaded 2×2 polymer waveguide switch array." Applied Optics 46.3 (2007): 379-383.

Wang et al., "Silicon photonic integrated circuit swept-source optical coherence tomography receiver with dual polarization, dual balanced, in-phase and quadrature detection." Biomedical Optics Express 6.7 (2015): 2562-2574.

Yaqoob et al., "Spectral domain optical coherence tomography: a better OCT imaging strategy." Biotechniques 39.6 (2005): S6-S13.

Yurtsever et al., "Photonic integrated Mach-Zehnder interferometer with an on-chip reference arm for optical coherence tomography." Biomedical Optics Express 5.4 (2014): 1050-1061.

Yurtsever et al., "Ultra-compact silicon photonic integrated interferometer for swept-source optical coherence tomography." Optics Letters 39.17 (2014): 5228-5231.

International Search Report and Written Opinion in International Patent Application No. PCT/US2021/016131 dated Apr. 22, 2021, 12 pages.

\* cited by examiner

CHIP-SCALE OPTICAL COHERENCE TOMOGRAPHY ENGINE

CROSS-REFERENCE TO RELATED APPLICATION(S)

This application claims the priority benefit, under 35 U.S.C. 119(e), of U.S. Application No. 63/003,956, which was filed on Apr. 2, 2020, and is incorporated herein by reference in its entirety.

BACKGROUND

Since its advent in the early 1990s, OCT has rapidly become a ubiquitous imaging technology for biomedical diagnosis and non-destructive testing (NDT) due to its unique capability to generate high-quality three-dimensional (3-D) images in a non-invasive manner. Nowadays, most mainstream OCT systems are in the so-called spectral domain (SD)-OCT configuration due to its sensitivity advantage (analogous to the Fellgett's advantage in the spectral domain). In SD-OCT, light from a spatially coherent broadband source (e.g., a superluminescent diode (SLD) or supercontinuum source) is split into two paths: (1) a reference arm with a fixed mirror and (2) a sample arm where the light illuminates and is backscattered by the sample. Reflected light from the two paths are combined and fed into a spectrometer.

Light scattered at different depths of the sample produces interference fringes with the reference beam with varying free spectral range (FSR), where a small FSR signals a large optical path length (OPL) difference between the reference arm and the backscattering source. The resulting spectrum contains a series of spectral-domain oscillations (fringes), each corresponding to the optical backscattering strength at a particular sample depth. A Fourier transform of the spectrum then generates a one-dimensional (1-D) depth profile of the sample. An alternative to SD-OCT is to use a wide-band tunable laser as the light source (swept-source OCT), which suffers from a higher cost, coarser axial resolution, and limited system ruggedness due to the delicate moving parts in the tunable laser.

Performance metrics of an SD-OCT system include imaging depth, axial resolution, sensitivity, A-scan line rate (each A-scan acquires a 1-D depth profile at one spatial location), lateral resolution, and field of view. The lateral resolution and field of view are usually determined by the scan lens and the imaging probe construction rather than the OCT engine.

The imaging depth of OCT depends on both the penetration depth of light in the sample as well as the optical resolution of the spectrometer (or sampling rate in the spectral domain). The penetration depth can be optimized by choosing suitable wavelengths for different samples. For instance, typical wavelength choices include 800-1000 nm for imaging eyes, 1300 nm or longer for more opaque tissue (e.g., skin), and even the mid-infrared (IR) range for NDT in highly scattering samples.

Spectrometer resolution $\delta\lambda$ is often a limiting factor for SD-OCT. In this case, the imaging depth range Z is given by:

$$Z = \frac{1}{2} \cdot \frac{\lambda^2}{\delta\lambda} \qquad (1)$$

In addition to limiting the imaging depth, the finite spectrometer resolution also inflicts sensitivity roll-off, also known as loss of OCT sensitivity with depth. The roll-off can be understood as follows: with larger imaging depth, the optical path length difference between the reference arm and the backscattering source increases. Consequently, the resulting spectrum contains spectral-domain oscillations with smaller FSRs. As the FSR approaches the spectrometer resolution limit, the SNR corresponding to the imaging depth drops due to the reduced contrast transfer of the spectral oscillations. In other words, the SNR becomes bounded by the spectral-domain modulation transfer function (MTF) of the spectrometer for a fixed reference arm length.

The axial resolution $I_c$ is dictated by the bandwidth BW of the light source or the spectrometer:

$$l_c = C \cdot \frac{\lambda^2}{BW} \qquad (2)$$

Here C is a constant that depends on the spectra of the light source or wavelength-dependent response of the spectrometer. Current OCT systems typically provide an axial resolution of a few microns, corresponding to a spectral bandwidth of approximately 100 nm for a center wavelength of 1300 nm.

The speed of an OCT measurement (the A-scan rate) is limited by both the SNR (and hence integration time at the detector) and the speed of the spectrometer or the wavelength-sweeping laser. When SNR is the limiting factor, sensitivity and speed pose a trade-off. State-of-the-art OCT systems typically operate with A-scan rates of the order of tens of kHz, with some ultrafast systems now offering multi-MHz scanning rates.

Finally, the sensitivity of an OCT measurement, defined as the minimum sample reflectivity that generates an SNR of unity, can be enhanced by suppressing the main noise sources. These noise sources include the photon shot noise, the relative intensity noise (RIN) of the light source, and the detector noise. While photon noise is limited by the system optical throughput and the detector integration time, the RIN and detector noise can be mitigated with improved optical engine design.

To overcome the poor size, weight, and power plus cost (SWaP-C) metrics of conventional OCT systems, silicon photonics has been explored as a solution to enable low-cost, portable OCT. To date, the work on silicon-photonic OCT systems can be roughly divided into two categories. In the first category, the goal is to replace a traditional spectrometer with an on-chip counterpart, such as an arrayed waveguide grating (AWG) or planar concave grating. The bandwidth of an integrated photonic spectrometer is typically limited by the operating bandwidth of its photonic components to a fraction of its center wavelength. For instance, a single properly designed AWG can operate over 10-15% fractional bandwidth, corresponding to 100-200 nm coverage near the telecom bands. It is also possible to cascade and juxtapose many AWGs (or other single spectrometers) to extend the bandwidth, although this approach comes at the expense of vastly increased system complexity and exacerbated signal-to-noise ratio (SNR) penalty. OCT systems in this first category tend to be hampered by the optical throughput penalty in dispersive spectrometers and their excessively large footprints (e.g., a 512-channel AWG occupies an on-chip area of 2.0 cm×2.7 cm).

In the second category of silicon-photonic OCT systems, the goal is to miniaturize the interferometer in the OCT system by integrating the reference arm and/or optical receiver on-chip. The SD-OCT systems in this category have reference arms with fixed OPLs. At least one report disclosed the use of a waveguide delay line for now-obsolete time-domain OCT. This waveguide delay line provided an OPL tuning range of less than 1 mm despite a long waveguide length. In this type of silicon-photonic OCT system, the on-chip optics are merely down-scaled versions of the bulk elements bringing little architectural innovation or optical performance boost.

SUMMARY

Here, we disclose a transformative single-chip OCT system based on silicon photonics technologies. This single-chip OCT system, also called a chip-scale OCT engine, may include one or more of the following three modules: (1) a digital Fourier-Transform (dFT) spectrometer, (2) a variable delay optical interferometer, and (3) a high-speed optical phased array (OPA) beam scanner. These modules can be integrated on the same chip or substrate, with each module offering a unique performance enhancement: the broadband dFT spectrometer offers superior signal-to-noise ratio (SNR) benefitting from the Fellgett's advantage, as well as fine axial resolution; the variable delay interferometer ensures large imaging depth by circumventing sensitivity roll-off, a major limitation of conventional spectral domain OCT systems; and the electro-optic OPA allows beam steering at speeds hundreds to thousands of times faster than mechanical scanners and does not need moving parts. A chip-scale OCT engine with these modules can be manufactured using CMOS microfabrication technologies developed in the integrated circuits (IC) industry. The resulting OCT engine has several advantages over other OCT systems, including: (1) a single-chip architecture eliminating complex assembly and alignment steps; (2) high performance rivaling or even exceeding benchtop OCT systems; and (3) scalable, low-cost manufacturing.

The on-chip dFT spectrometer overcomes a major limitation plaguing other miniature spectrometers—their much inferior performance compared to benchtop spectrometers due to the linear scaling law, which dictates that the spectrometer performance scales linearly with its size. Unlike a spectrometer that relies on an optical grating to separate different wavelengths, a dFT spectrometer employs a unique optical switch network to retrieve spectral information. Unlike a grating-based spectrometer, the dFT spectrometer follows an exponential scaling law—its performance doubles with every new optical switch added to the network, thereby delivering unprecedented high performance with a small on-chip footprint. Moreover, it also benefits from Fellgett's advantage, which provides a significant SNR edge over conventional dispersive spectrometers when analyzing broadband signals, such as in the case of OCT. Processing the output of the dFT spectrometer with a spectrum reconstruction algorithm doubles the spectral resolution compared to the classical textbook Rayleigh limit.

An inventive OCT system comprises a light source, a beam splitter, a reference arm, a sample arm, and a digital Fourier transform (dFT) spectrometer. In operation, the light source emits a broadband beam, which the beam splitter splits into a reference beam and a probe beam. The reference arm delays the reference beam, and the sample arm illuminates a sample with the probe beam and collects light scattered and/or reflected by the sample in response to the probe beam. The dFT spectrometer measures a spectrum of an interference pattern formed by the reference beam and the light scattered and/or reflected by the sample.

The beam splitter, the reference arm, the sample arm, and the dFT spectrometer can be integrated on a substrate along with a beam-steering device that steers the probe beam across the sample and receives the light scattered and/or reflected by the sample.

The reference arm can comprise a switchable delay line. This switchable delay line may include an optical switch switchable between a first state and a second state, a first waveguide with a first optical path length, and a second waveguide with a second optical path length different than the first optical path length. The first waveguide produces a first time delay when the optical switch is in the first state. The second waveguide produces a second time delay different than the first time delay when the optical switch is in the second state.

The dFT spectrometer may include a second beam splitter to split incident light into a first portion and a second portion. A first interference arm, in optical communication with this second beam splitter, receive the first portion of the incident light. Like with switchable delay line, this first interference arm includes a first optical switch switchable between a first state and a second state, a reference waveguide having a first waveguide length to produce a first delay, and a variable waveguide having a second waveguide length to produce a second delay different than the first delay. The reference waveguide receives the first portion of the light when the optical switch is in the first state, and the variable waveguide receives the first portion of the light when the optical switch is in the second state. A second interference arm, in optical communication with the second beam splitter, to receive the second portion of the incident light. And a detector, in optical communication with the first interference arm and the second interference arm, detects interference of the first and second portions of the incident light.

The dFT spectrometer may further comprise a phase modulator, in optical communication with the second beam splitter, to modulate a relative phase between the first portion and the second portion such that interference of the first portion with the second portion creates a null at a desired wavelength. This desired wavelength can be a center wavelength of the broadband beam. The dFT spectrometer can make a plurality of interferogram measurements between the first portion and the second portion with a null at the desired wavelength in each interferogram measurement in the plurality of interferogram measurements.

The OCT system may also include a waveguide-integrated photodetector, in optical communication with an output of the dFT spectrometer, to detect an output of the dFT spectrometer. It may include an electro-optic modulator, operably coupled to the sample arm, to modulate the probe beam at a reference frequency. And it may include a lock-in amplifier, operably coupled to the waveguide-integrated photodetector, to measure a component of an output of the dFT spectrometer whose frequency is locked to the reference frequency.

An OCT engine with a dFT spectrometer, which includes arms comprising cascaded optical switches, can be used to perform OCT as follows. The cascaded optical switches can be set to a first setting in a plurality of settings, where each of the plurality of settings produces a different path length difference between the arms of the spectrometer. Then the probe beam is scanned across the sample, and light scattered and/or reflected by the sample in response to the probe beam is collected. This scattered and/or reflected light and a reference beam are coupled into the spectrometer, which interferes them to produce interference that is detected at an output of the spectrometer.

The spectrometer can be integrated on a substrate with an OPA, in which case the OPA can scan the probe beam across the sample (and collect the light scattered and/or reflected by the sample). There may also be a switchable delay line integrated on a substrate with the spectrometer (and the optional OPA). In this case, the switchable delay line delays the reference beam by a first delay before the reference beam is coupled into the spectrometer. In addition, after detecting interference of the reference beam and the light scattered and/or reflected by the sample for each of the plurality of settings of the cascaded optical switches, the switchable delay line can be set to delay the reference beam with respect to the probe beam by a second delay different than the first delay. In this case, the scans and interference generations and detections are repeated for each of the plurality of settings of the cascaded optical switches in the spectrometer.

The probe beam can be modulated at a reference frequency, in which case a lock-in amplifier may measuring a component of the interference of the reference beam and the light scattered and/or reflected by the sample at the reference frequency. A processor or other device may form a volumetric image of the sample based on the interference of the reference beam and the light scattered and/or reflected from the sample. If scanning the probe beam across the sample comprises angularly dispersing the probe beam, then the processor can compensate angular dispersion of the probe beam when forming the volumetric image.

An integrated OCT engine may include a substrate, beam splitter, switchable delay line, modulator, OPA, dFT spectrometer, photodetector, and lock-in amplifier. The beam splitter is integrated on the substrate and splits a broadband beam from a light source (e.g., a superluminescent diode) into a reference beam and a probe beam. The switchable delay line is integrated on the substrate in optical communication with the beam splitter and delays the reference beam with respect to the probe beam. The modulator is integrated on the substrate in optical communication with the beam splitter and modulates the probe beam at a reference frequency. The OPA is integrated on the substrate in optical communication with the beam splitter and may include one or more electro-optic switches or phase shifters. The OPA illuminates a sample with the probe beam and collects light scattered and/or reflected by the sample in response to the probe beam. The dFT spectrometer is integrated on the substrate in optical communication with the reference arm and the sample arm and may include one or more thermo-optic switches or phase shifters. It measures a spectrum of an interference pattern formed by the reference beam and the light scattered and/or reflected by the sample. The photodetector is integrated on the substrate in optical communication with the dFT spectrometer and detects an output of the dFT spectrometer. And the lock-in amplifier, which is operably coupled to the photodetector, measures a spectral component of the output of the dFT spectrometer whose frequency is locked to the reference frequency.

All combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. Terminology explicitly employed herein that also may appear in any disclosure incorporated by reference should be accorded a meaning most consistent with the particular concepts disclosed herein.

BRIEF DESCRIPTION OF DRAWINGS

The drawings are primarily for illustrative purposes and are not intended to limit the scope of the inventive subject matter. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Here we disclose a chip-scale optical coherence tomography (OCT) engine that uses a broadband digital Fourier Transform (dFT) spectrometer to attain fine spatial resolution, a variable delay line to attain large imaging depth, and an optical phased array (OPA) for high-speed (e.g., MHz or GHz rate) beam scanning. This dFT-based OCT engine can be used to make an OCT system that operates with enhanced sensitivity and A-line scan rate of 1 MHz, with higher scan rates possible. The sensitivity can be further enhanced by a using a lock-in amplifier to eliminate long-term drift and 1/f noise. Unlike conventional spectral-domain (SD) OCT systems, a dFT-based OCT system can operate with little to no degradation in sensitivity with depth thanks to a tunable on-chip delay line. A dFT-based OCT system with a 1024-channel dFT spectrometer and wavelength band spanning 1250 nm to 1350 nm can operate with an imaging depth of 8.6 mm (in air) and an axial resolution of 7.4 μm (again, in air). All of these performance metrics are significantly better than those of comparable SD-OCT systems.

Figure 1A:
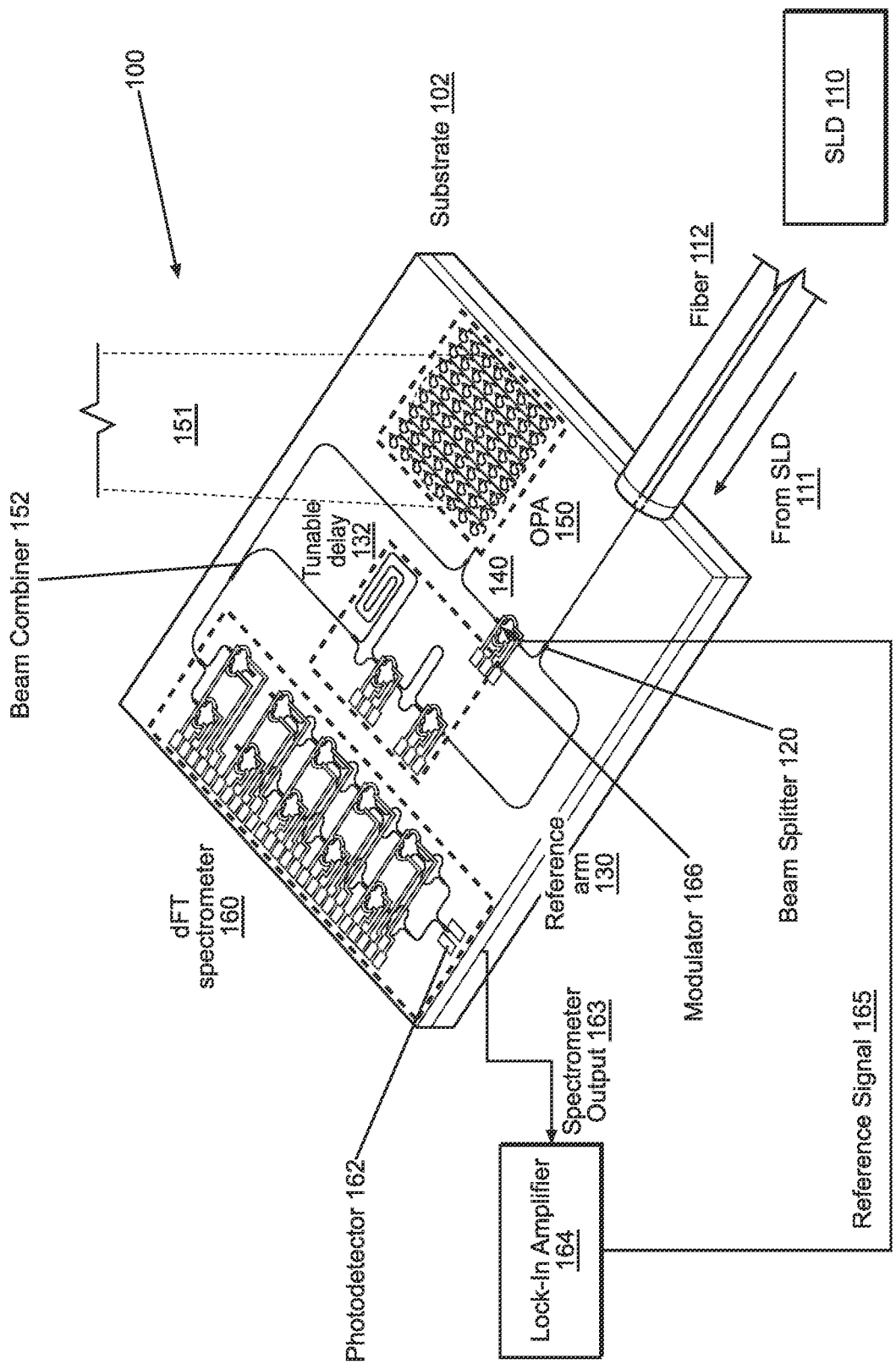
FIG. 1A shows a chip-scale OCT optical engine with a digital Fourier transform (dFT) spectrometer and an optical phased array (OPA).

Chip-Scale OCT Engines with High Speed, Enhanced Sensitivity, and Large Imaging Depth FIG. 1A shows a perspective view of a single-chip OCT engine 100 fabricated in a single chip or substrate 102. This OCT engine 100 is coupled to a broadband light source 110, such as a superluminescent diode (SLD), that emits a broadband beam 111 into an optical fiber 112 that is coupled to a waveguide in the substrate 102. The fiber 112 launches this broadband beam 111 into the waveguide, which guides it to a 1×2 beam splitter 120 that splits the broadband beam 111 into a reference beam and a sample beam. The reference beam propagates through a reference arm 130 and the sample beam propagates through a sample arm 140.

Unlike in a conventional OCT interferometer, which has a static reference arm, the reference arm 130 in this OCT engine 100 includes a tunable on-chip delay line 132 comprising cascaded optical switches whose outputs are couple to waveguides of different lengths, a design derived from the dFT spectrometer architecture (described below). Opening and closing the switches, which can be implemented as 1×2 or 2×2 thermo-optic switches with low insertion losses, changes the optical path length of the tunable on-chip delay line 132 and hence of the reference arm 130. Setting the switches appropriately causes the tunable delay line 132 to balance the path length difference between the reference arm 130 and the sample arm 140 for different sample lengths (or depths into the sample itself). Balancing these path lengths avoids or reduces the need to sample high-frequency spectral fringes and thereby reduces or eliminates sensitivity roll-off—a phenomenon causing severe SNR degradation with increasing sampling depth in traditional OCTs.

The digital delay line 132 has a series of cascaded switches route light sequentially into paths with OPL differences of powers of two times ΔL. Compared to traditional thermo-optic (TO) waveguide delay lines, the design provides large true-time delay commensurate with OCT imaging depth. The tunable delay line balances the optical path length (OPL) difference between the reference arm 130 and the sample arm 140. This reduces or eliminates sampling of spectral fringes with small free spectral ranges (FSRs) and can thereby eliminate the sensitivity roll-off entirely.

The sample arm 140 includes an on-chip OPA 150 that scans the sample beam 151 transversely across the sample (e.g., a person's eye or skin; not shown). The OPA 150 includes one or more waveguides that guide the sample beam to an array of antenna elements that couple the sample beam 151 out of the substrate 102 and couple light scattered by the sample back into the substrate 102. The OPA 150 also includes electro-optic and/or thermo-optic phase shifters that modulate the phases of the beams coupled into and out of the substrate via the antenna elements. Tuning the drive voltage(s) applied to these phase shifters steers the sample beam 151 laterally across the sample. The phase shifters can also be modulated to produce a particular spatiotemporally varying far-field beam pattern on or in the sample. If the phase shifters are electro-optic phase shifters, the beam can be scanned (or the pattern can be modulated) at Megahertz or Gigahertz rates—hundreds to thousands of times faster than mechanical beam scanners.

The high-speed OPA 150 enables a new OCT scan modality, where transverse spatial scanning (B-scan) is executed before acquisition of a complete depth or spectral profile (A-scan). In conventional OCT, many one-dimensional scans (A-scans) are performed at several depths to create a two-dimensional image (B-scan or tomogram). Those B-scans, if acquired closely and rapidly, can be translated into a volumetric image (C-scan) of a retina, for example. In Cartesian coordinates, the A-scans represent variations along the z axis (the system's optical axis). The B-scans represent either x-z or y-z slices, depending on whether the beam is scanned faster along the x axis or the y axis. And C-scans represent complete x-y-z information. Because the OPA 150 can scan so quickly, the chip-scale OCT engine 100 can acquire scans in the x or y direction faster than it can acquire scans in the z direction. Put differently, it can acquire a first lateral scan in a particular lateral dimension (e.g., the x dimension) at a first depth (e.g., $z_1$), then a second lateral scan in the same lateral dimension at a second depth (e.g., $z_2 > z_1$), and so on until an entire B-scan is acquired. Other coordinate systems does not have to be Cartesian; the OPA 150 can scan the sample beam 151 laterally in any of a variety of patterns, including raster-scan patterns, spirals, concentric circles, or even discrete points.

The OPA 150 couples light scattered from the sample back into the sample arm 140, where it is guided by one or more integrated waveguides to one input port of a 2×1 or 2×2 beam combiner 152. The other input port of the beam combiner 152 receives the delayed reference beam from the reference arm 130. The beam combiner 152 couples the reference beam and the scattered light into the dFT spectrometer 160, which can be implemented as a Mach-Zehnder interferometer. At least one of the arms in this interferometer includes a series of cascaded optical switches connected by two (or more) waveguides of different lengths. Each optical switch directs the incident light into one waveguide or another, thereby changing the optical path length difference between the first interference arm and the second interference arm.

The switches in the dFT spectrometer 160 can include thermo-optic phase shifters, electro-optic phase shifters, or a combination of thermo-optic and electro-optic phase shifters. Thermo-optic phase shifters tend to have low insertion loss and slow switching speeds (e.g., about 10 kHz), whereas electro-optic phase shifters tend to have higher insertion loss and faster switching speeds (e.g., about 1 GHz, 10 GHz, or higher). Using thermo-optic phase shifters in some stages and electro-optic phase shifters in other stages of the dFT spectrometer 160 allows for optimization between speed and insertion loss. Alternatively, the dFT spectrometer 160 may be optimized for low insertion loss with mainly or only thermo-optic phase shifters (i.e., few or no electro-optic phase shifters). Even with slow thermo-optic phase shifters in the dFT spectrometer 160, the OCT engine 100 can still acquire data at video frames by scanning transversely at MHz or GHz rates with the OPA 150, then stepping through different depths more slowly by switching the thermo-optic phase shifters in the dFT spectrometer 160 as described in greater detail below with respect to FIG. 6.

The output of the dFT spectrometer 160 is coupled to a silicon-photonic, waveguide-integrated photodetector 162 that senses the broadband interference fringes or interferograms generated by the dFT spectrometer 160. The waveguide-integrated detector 162 may drastically outperform its traditional bulk counterparts in terms of both SNR and speed. In the waveguide-integrated detector 162, light is efficiently funneled to the active volume of detector 162 via a high-index-contrast Si waveguide rather than from free space, enabling the detector's active volume to be reduced with proportionally decreased noise. This waveguide-integrated photodetector 160 may feature an exceptionally large 3-dB bandwidth (e.g., exceeding 40 GHz). Therefore, unlike traditional OCT detectors, which operate in a direct current (DC) mode, the silicon photonic OCT receiver 162 emits an alternating-current (AC) spectrometer output 163 that can readily support lock-in measurements at a high frequency to eliminate low-frequency noise, including 1/f noise.

In this case, the electronic-domain spectrometer output 163 is coupled to a lock-in amplifier 164, which drives an electro-optic modulator 166 in the sample arm 140 with a reference signal 165. This reference signal 165 may be a sinusoid at a particular reference frequency. The lock-in amplifier 164 locks to the component of the output signal 163 from the dFT spectrometer 160 that oscillates at that reference frequency, filtering out the DC background in the output signal. Lock-in detection of the reference signal 165 in the spectrometer output 163 by the lock-in amplifier 164 contributes to signal extraction in the presence of sample optical loss or reflectivity variations. In traditional OCT, variations in sample loss or reflectivity cause a power imbalance between the reference and the sample arms. This power imbalance can compromise the spectral-domain fringe visibility and hence reduce the SNR. In contrast, lock-in detection measures only the AC component at the modulated frequency (the frequency of the reference signal 165) and can effectively reject the DC background when a large arm imbalance is present.

Figure 1B:
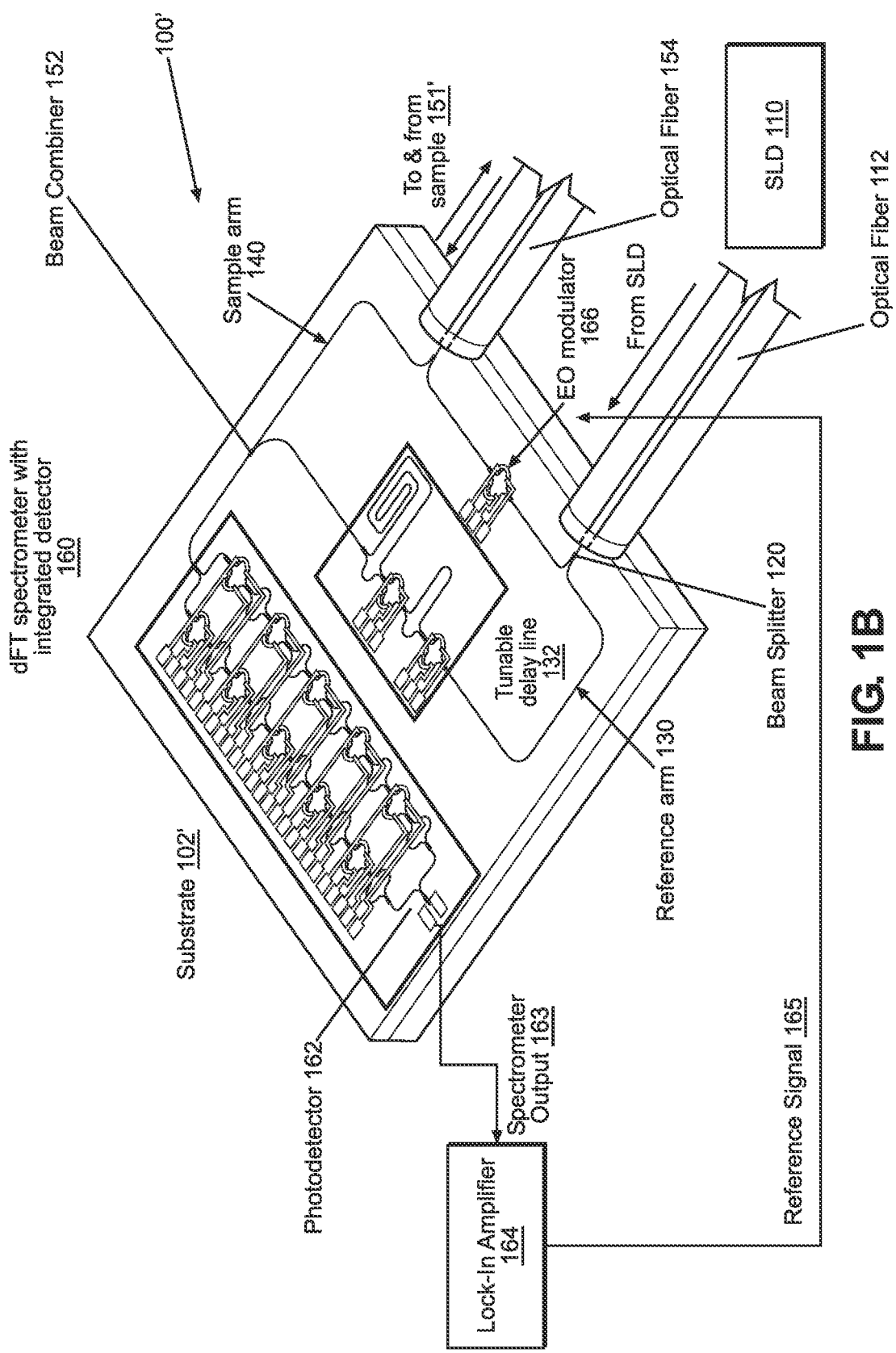
FIG. 1B shows a chip-scale OCT optical engine with a dFT spectrometer and an off-chip beam scanner.

FIG. 1B shows an SD-OCT engine 100' without an integrated OPA 150. Like the OCT engine 100 in FIG. 1A, this modified OCT engine 100' includes a beam splitter 120, reference arm 130, sample arm 140, dFT spectrometer 160, and electro-optic modulator 162 integrated onto a single substrate 102. An optical fiber 112 couples light from a broadband light source, such as an SLD 110, into a waveguide that is integrated into the substrate 102 and that guides the light to the beam splitter 120. The beam splitter 120 splits the incident light into a reference beam, which is coupled into the reference arm 130, and a probe beam 151', which is coupled into the sample arm 140, just as in FIG. 1A. In this case, however, the probe beam 151' propagates to the sample (not shown) via another optical fiber 154, which guides the probe beam to the sample. A 2-D beam scanner (e.g., a mechanical galvanometer; not shown) coupled to the optical fiber 154 scans the probe beam across the sample surface and redirects scattered and/or reflected light back into the sample arm 140 via the optical fiber 154 that guides the probe beam 151'. The sample arm 140 guides this scattered and/or reflected light to the beam combiner 152, which combines the scattered and/or reflected light with the reference beam, which is time-delayed by the tunable delay line 132 in the reference arm 130. The two beams interfere with each other as they propagate through the dFT spectrometer 160, which measures the interference as described above with respect to FIG. 1A and below with respect to FIG. 2.

The OCT engine 100' in FIG. 1B can be coupled to other types of sampling mechanisms, not just optical beam scanners. For example, the fiber 154 can be coupled to an array of sample arms coupled with an array of optical probing channels (e.g., waveguides, fibers, and/or free-space optical elements) to collect backscattered light from different locations simultaneously or sequentially. Some or all of the optical probing channels could also be integrated into the substrate 102. Optical switches or beam deflectors may be used to couple portions of the probe beam 151' from the optical fiber 154 into the different probe channels. (The OPA 150 in FIG. 1A can be used to probe multiple areas simultaneously or sequentially.) Similarly, optical switches or beam deflectors may be used to choose the probe channel to be combined with the reference beam in the reference arm 130 after signal collection. A multi-channel engine can significantly increase the B-scan rate and system ruggedness by (partially) replacing the mechanical galvanometer scanning mechanism with electro-optic or thermo-optic switches, which re-route light between different output channels without moving parts.

The OCT engines 100 and 100' in FIGS. 1A and 1B, respectively have significantly better sensitivity and SNR than state-of-the-art OCT engines thanks to the low noise and high speed of on-chip photodetectors on top of Fellgett's advantage. TABLE 1 below benchmarks the performance of a dFT-based OCT engine like the one in FIG. 1B against a commercial benchtop OCT system (in this case, a high-speed, high-resolution SD-OCT TEL320C1 from Thorlabs). Both systems operate in the 1300 nm wavelength band. The numbers in TABLE 1 are calculated based on a 1,024-channel dFT spectrometer used in conjunction with an off-the-shelf SLD source with a spectral width of 100 nm. The component insertion loss and detector performance are computed according to the specifications provided by the AIM Photonics PDK component library version 3.0a. The comparison demonstrates the advantages of the inventive OCT engine in imaging depth, speed, and sensitivity in addition to its apparent size, weight, power, and cost (SWaP-C) benefits. The axial resolution is dictated by the light source bandwidth and can be extended through coupling an extended broadband SLD (or a supercontinuum source) with the broadband dFT design.

TABLE 1

Performance comparison of dFT-based and commercial OCT systems

| System | Imaging depth (air) | Axial resolution (air) | Lateral Resolution | A-scan line rate | Sensitivity (max.) | Sensitivity roll-off |
|---|---|---|---|---|---|---|
| TEL320C1 | 3.5 mm | 5.5 μm | 13 μm | 146 kHz | 91 dB | Up to 9.5 dB |
| dFT-based OCT Engine | 8.6 mm | 7.4 μm | 15 μm | Up to 10's of MHz | 86 dB | Negligible |

Photonic integrated circuit (e.g., silicon photonics) technologies also open up exciting opportunities of integrating new functionalities and detection modalities within a chip-scale OCT system. For instance, new sensing modes including complex-conjugate suppressed full-range OCT, polarization diversity detection, and polarization-sensitive OCT have been demonstrated by combining coherent silicon photonics receivers with standard OCT systems. A dFT-based OCT platform can leverage latest advances in integrated photonics and electronics to enable scalable performance growth.

The OCT engines 100 and 100' in FIGS. 1A and 1B can also be used for optical coherence reflectometry (OCR), where a single A-scan at one spatial location is adequate (i.e., no two-dimensional (2-D) scanning). OCT technology is useful for instance for characterizing the eye axial length. Since 2-D mapping is not necessary, OCR can operate with a much smaller A-scan rate. An OCR engine can use SiN instead of silicon-on-insulator (SOI) as the photonic material platform, and thermo-optic switches in place of the electro-optic switches for higher optical throughput. The use of a SiN platform further allows OCR operation at shorter wavelengths (e.g., 850 nm).

A Broadband dFT Spectrometer for a Chip-Scale OCT Engine

Figure 2:
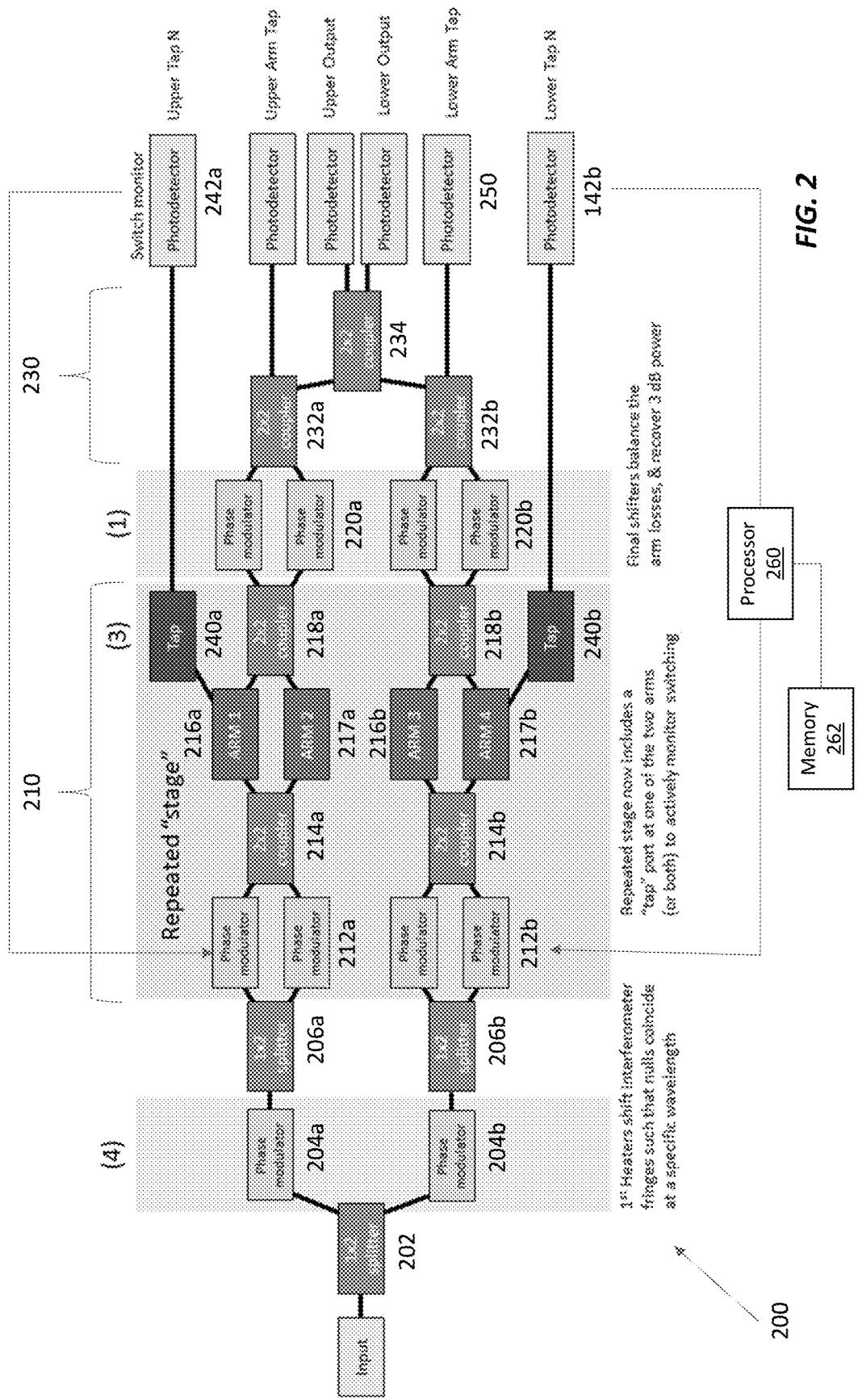
FIG. 2 shows a digital Fourier transform (dFT) spectrometer for use in an OCT engine with fine spectral resolution.

FIG. 2 shows a block schematic of a high-performance dFT spectrometer 200 suitable for use in a chip-scale SD-OCT system (e.g., the OCT engine 100 in FIG. 1A). This dFT spectrometer 200 includes an input splitter 202 that couples an input beam into two parallel paths. Each path has one or more binary delay stages 210 arranged in series (FIG. 2 shows only one stage 210 per path for clarity). Each binary delay stage 210 has two arms, shown in FIG. 2 as upper and lower arms, with a broadband switch at the input to each arm. In FIG. 2, each switch is implemented as a 1×2 coupler 206a, 206b whose outputs are coupled to respective phase modulators 212a, 212b, which in turn are coupled to inputs of respective 2×2 couplers 214a, 214b (collectively, phase modulators 214). Adjusting the relative phases of the inputs to the 2×2 couplers 214 varies the output power distribution at the outputs of the 2×2 splitters 214. By choosing the relative phase appropriately (e.g., 0 or π for perfect components), it is possible to switch an input light completely from one output to the other output. (Each switch can be implemented with a single phase modulator but using two phase modulators per switch enables less phase modulation per phase modulator (e.g., π/2 per phase modulator for net π phase shift) for more precise phase modulation than using a single phase modulator.)

Each broadband switch couples light into an upper arm 216a, 216b and/or into a lower arm 217a, 217b whose optical path length is different than that of the corresponding upper arm 216a, 216b. Each broadband switch may couple all of the light into one arm or the other, as in our original dFT spectrometer, or it may couple some light into each arm, which we call "partial switching." In either case, output couplers 218a, 218b couple light from the upper arms 216a, 216b and lower arms 217a, 217b to a beam-combining stage 230, which has cascaded 2×2 couplers 232a, 232b, and 234 that combine the outputs for detection by one or more photodetectors 250.

The light from the different arms interferes at the photodetectors 250, which are coupled to a processor 260. The measured interference pattern depends on the spectrum of the input beam and the path length difference(s) between and within each path through the dFT spectrometer 200. The processor 260 actuates the switches in the delay stages 210 based on settings stored in a memory 262. Actuating the switches changes the path length difference(s), making it possible to make interference measurements at many possible path length differences. The number of possible path length differences equals the number of measurable spectral channels. The processor 260 determines the spectrum based on these interference measurements by the photodetectors 250. The processor 260 also monitors and controls the tap monitor photodetectors, input phase modulator, output phase modulators, and switches described below using settings stored in the memory 262.

The dFT spectrometer 200 includes several additional features. To start, it has an optional phase modulator 204a, 204b (collectively, input phase modulators 204) at the input to each path through the dFT spectrometer 200 for narrowband filtering. These phase modulators 204 can be implemented as thermo-optic heaters that change the optical path length distance by heating a section of waveguide. The dFT spectrometer 200 can include two phase modulators 204—one in each path—as in FIG. 2 or a single input phase modulator 204 in one path and can placed at the path input(s) as in FIG. 2 or at the path output(s) (e.g., between couplers 232a, 232b and 234).

In either case, the input phase modulator(s) 204 introduce a relative phase shift that can be selected to produce a null in the detected interference spectrum. The center wavelength of this null depends on the relative phase shift and can be selected to selectively filter light at certain frequencies. For instance, it can be used to suppress interference at the wavelength of a strong signal, such as a Raman pump beam, that might otherwise dominate the spectrum measured by the spectrometer. This narrowband filtering is discussed in greater detail below.

In addition to in-line input phase modulators 204 for narrowband filtering, the dFT spectrometer includes taps 240a, 240b (collectively, taps 240) in each delay stage 210 for monitoring the switching efficiency. Each tap 240a, 240b couples a small fraction (e.g., 1% or less) of the beam propagating through one arm of the delay stage 210 to a corresponding photodetector 242a, 242b, which measures the tapped optical power. This measurement can be used to determine if the broadband switches are set correctly and to adjust the switch settings by change the relative phase differences imparted by the phase modulators 212a, 212b.

The dFT spectrometer 200 also includes a final amplitude modulation stage, implemented here with output phase modulators 220a and 220b (collectively, output phase modulators 220) coupled between the outputs of the output couplers 218a, 218b and the first set of 2×2 couplers 232a, 232b in the beam-combining stage 230. These output phase modulators 220a and 220b compensate for loss imbalances between the two arms by actively attenuating the optical signal as described in greater detail below.

The dFT spectrometer can be built with an unprecedented half-octave bandwidth. This bandwidth can run from 1200 nm to 1700 nm, covering all telecom bands (O, E, S, C, L and U bands) in a single device. The dFT spectrometer also features a spectral resolution of 0.12 nm or finer (with spectrum reconstruction), and a noise floor down to −70 dBm. The spectrometer can be packaged with bonded optical fibers and custom electronics to form a standalone, ready-to-use module. The module may offer performance comparable to a state-of-the-art benchtop optical spectrum analyzer (OSA). Its applications include laser and optical component testing and optical network monitoring with its significant size, weight, power, and cost (SWaP-C) advantages.

An ultra-broadband version of the dFT spectrometer 200 in FIG. 2 builds on two features: wavelength-insensitive adiabatic components and spectrally segmented modulation. These features promise spectrometer designs with even wider bandwidth. In practice, the bandwidth may ultimately be bounded by the transmission window of single-mode fibers and cut-off wavelength of the detector in the dFT spectrometer.

Figures 3A, 3B, 3C, 3D:
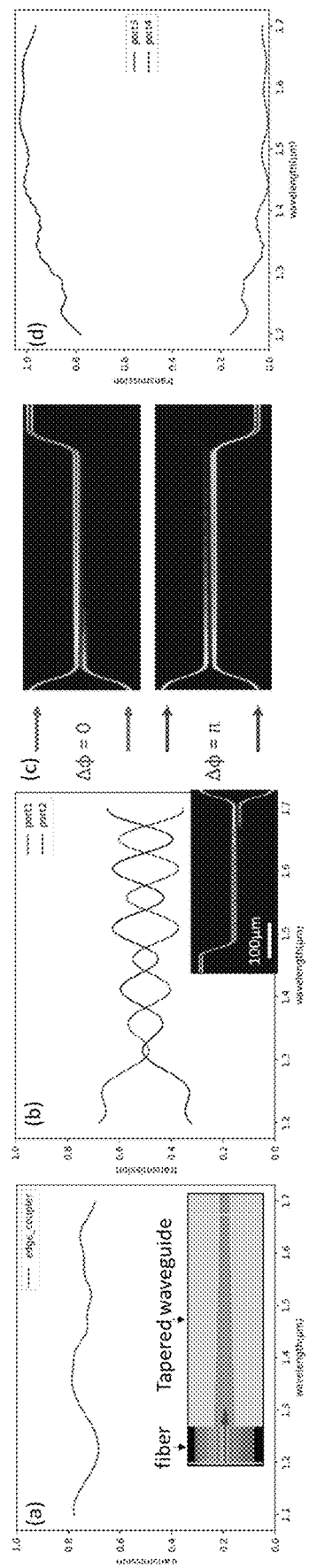
FIG. 3A shows a 1200-1700 nm broadband edge coupler suitable for use in a dFT spectrometer.
FIG. 3B shows a 1200-1700 nm broadband adiabatic 1×2 splitter suitable for use in a dFT spectrometer.
FIG. 3C shows a 1200-1700 nm broadband adiabatic 2×2 coupler for optical routing suitable for use in a dFT spectrometer.
FIG. 3D is a plot of the adiabatic 2×2 coupler in FIG. 3C as a function of wavelength.

FIGS. 3A, 3B, and 3C show dFT components designed to cover the 1200-1700 nm regime, including a fiber-to-waveguide inverse taper coupler, adiabatic 1×2 splitter/combiner, and 2×2 couplers connecting switch stages, respectively. FIG. 3D is a plot illustrating the broadband operation of the 2×2 coupler in FIG. 3C.

FIG. 3D shows simulated responses of a 1,024-channel dFT spectrometer constructed using the components in FIGS. 3A-3C. The simulation first uses finite-difference time-domain (FDTD) to model the individual elements, followed by computing the entire device response with a rigorous S-matrix approach. While the splitters and couplers are all broadband, the Mach-Zehnder interferometer (MZI)

optical switches have a bandwidth limited by the 1/λ dependence of optical phase delay imparted by the thermo-optic (TO) phase shifters.

By driving the TO phase shifters at different voltages, it is possible to tune the "perfect" switching wavelength (where light is completely routed into one waveguide with no power entering the other) across the 1200-1700 nm range. Near the "perfect" switching wavelength, the dFT spectrometer behaves as a simple MZI with unbalanced arm lengths. Transmission near the "perfect" switching wavelength thus exhibits a "locally regular" sinusoidal fringe pattern with close-to-unity amplitude modulation (i.e., high fringe visibility). The period of these fringes is precisely determined by the optical path length (OPL) difference between the dFT arms. Sweeping the driving voltage spectrally shifts the highly regular and visible fringes across the 1200-1700 nm band, and hence the name "spectrally segmented modulation". Therefore, by recording the spectra at multiple driving voltages for each OPL difference, the ensemble of measured transmission spectra forms a linearly independent basis set that can be used to reconstruct arbitrary broadband input spectrum. Spectral resolution across the entire 1200-1700 nm band remains the same as a narrowband dFT device with the same maximum OPL difference, as fine spectral features are resolved by the "locally regular" fringes.

Figures 4A, 4B:
FIG. 4A shows simulated transmission spectra at effective refractive index differences of 0.0325 (upper plot), 0.03875 (middle plot), and 0.0425 (lower plot) for a 10-switch dFT spectrometer (top) actuated to provide an 80 μm optical path difference (OPD).
FIG. 4B shows simulated transmission spectra at effective refractive index differences of 0.0325 (upper plot), 0.03875 (middle plot), and 0.0425 (lower plot) for a 10-switch dFT spectrometer (top) actuated to provide a 40,920 μm optical path difference (OPD).

FIGS. 4A and 4B show simulated spectra from a 10-switch (delay stage) dFT spectrometer where the switches are driven with spectrally segmented modulation (EC: Edge coupler. PD: Photodetector). The top of each figure shows the dFT spectrometer and its switch state. The bottom panels of FIGS. 4A and 4B correspond to different switch driving voltages such that perfect switching occurs at wavelengths of 1300 nm, 1550 nm, and 1700 nm.

In FIG. 4A, only one switch is actuated to produce a nominal optical path difference between the spectrometer arms of 80 μm; in FIG. 4B, all of the switches are actuated to produce a nominal optical path difference between the spectrometer arms of 40,920 μm. Thanks to wavelength dispersion and waveguide dispersion, the actual switch state varies with wavelength and temperature. To compensate for dispersion, the heaters in the switches can be set to higher or lower temperatures, resulting in slight changes in the effective refractive index and hence different switching ratios for the switches over different spectral segments. These switch settings and switching ratios can be set empirically to maximize the fringe visibility over a particular wavelength range (spectral segment). In FIGS. 4A and 4B, for instance, increasing the effective refractive index, which is equivalent to increasing the temperature of the thermo-optic heater in each switch, increases the center wavelength of the spectral segment with the highest fringe visibility.

For more on dFT spectrometers, please see U.S. Pat. No. 10,006,809, entitled "Apparatus, Systems, and Methods for On-Chip Spectroscopy Using Optical Switches," or U.S. Pre-Grant Publication No. 2020/0256728 A1, entitled "High-Performance On-Chip Spectrometers and Spectrum Analyzers," each of which is incorporated herein by reference in its entirety.

An Optical Phased Array for On-Chip Beam Steering

Figure 5A:
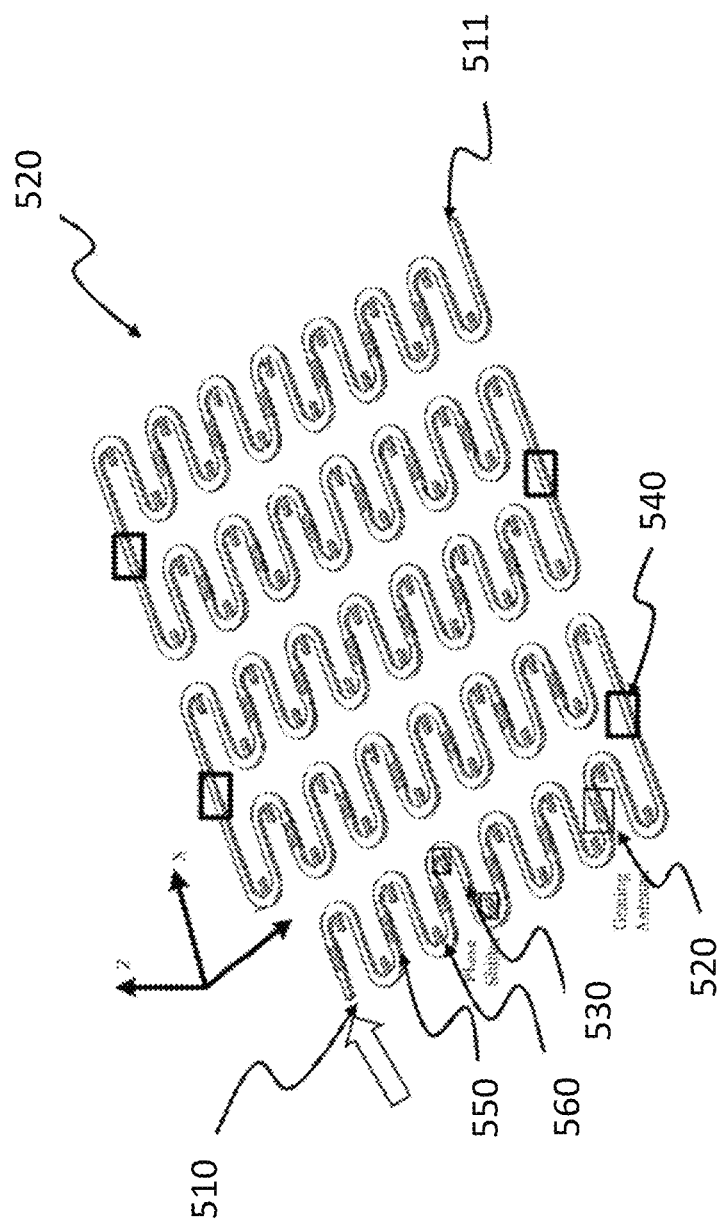
FIG. 5A shows a serpentine OPA with electro-optic phase shifters suitable for use in a chip-scale OCT optical engine.

FIG. 5A illustrates an optical phased array (OPA) 500 suitable for use as the OPA 150 in the OCT engines 100 and 100' of FIGS. 1A and 1B, respectively. The OPA 500 includes an array of grating antenna 520 and phase shifter 530 pairs that are connected by a series of waveguides 550. These waveguides 550 have an input 510 and an output 511 connected by waveguide bends 560 and parallel waveguide section 540. The grating antennas 520, phase shifters 530, and waveguides 550 are arranged in a close-packed, multi-section serpentine shape, effectively arraying the grating antennas 520 on a rectangular grid with equal or unequal spacing between adjacent grid points. The grating antennas 520, phase shifters 530, and waveguides 550 components can be made on a single optical chip (e.g., substrate 102 in FIGS. 1A and 1B) on any suitable optical wave-guiding material platform, including silicon-on-insulator (SOI), silicon nitride, doped silicon oxide, indium phosphide, etc. In particular for an SOI platform, the chip can be made by complementary metal-oxide-semiconductor (CMOS) fabrication processes.

The spacings or pitch between adjacent grating antennas 520 in the transverse (x or y) directions are generally between 5 μm to 20 μm and can be equal or unequal. An unequally spaced antenna grid or sparse array may provide better side lobe suppression in far field optical patterns generated by the OPA 500. The bending radii of the waveguide bends 560 and the lengths of the waveguide sections 540 can be chosen to provide the desired grid spacing or pitch. The waveguides 550 can include taper structures that connect to the grating antennas 520 and phase shifters 530, which may have different waveguide widths.

Each waveguide phase shifter 530 can be implemented as an electro-optic or thermo-optic phase shifter. An electro-optic phase shifter includes a waveguide section made of electro-optic material between a pair of electrodes. Applying a voltage to the electrodes creates an electric field across the electro-optic material, changing the local refractive index of the waveguide section. A thermo-optic phase shifter includes electrodes that are coupled directly a resistive section of the waveguide or to a resistive heater next to the waveguide section. Passing a current through the resistive section or heater via the electrodes causes the waveguide section to heat up, producing a local refractive index change. In both cases, the local refractive index change modulates the phase of the light passing through the waveguide section. Electro-optic phase shifters tend to be faster than thermo-optic phase shifters (e.g., they can modulate light at MHz or GHz raters instead of kHz rates) and so can be used in OPAs and OCT engines where fast scanning is desired.

The grating antennas 520 couple light (e.g., probe beam 151/151' in FIG. 1A/1B) out of the waveguide 550 and toward the sample, which is usually in the far field of the OPA 500. The beams interfere in the far field to produce a pattern, such as a spot, on the sample surface. Adjusting the phase modulation imparted by the phase shifters 530 causes this far-field pattern to change. In the case of a spot, the phase modulation may cause the spot to scan across the surface in a raster pattern or spiral at a rate determined in part by the modulation speed of the phase shifters 530.

The grating antennas 520 couple light out of the waveguide 550 at angles proportional to their grating period(s) and the wavelength of the probe beam. Since the probe beam for OCT has a very broad bandwidth, e.g., 100 nm or more, this angular dependence causes the emitted probe beams to spread over an angular range, with longer wavelengths diffracted by larger angles than shorter wavelength. If the far-field pattern is a spot, this wavelength-dependent diffraction smears the spot in the transverse dimension. More generally, the wavelength-dependent diffraction can be treated as creating a superposition of far-field patterns that are scaled and shifted in proportion to wavelength.

Figure 5B:
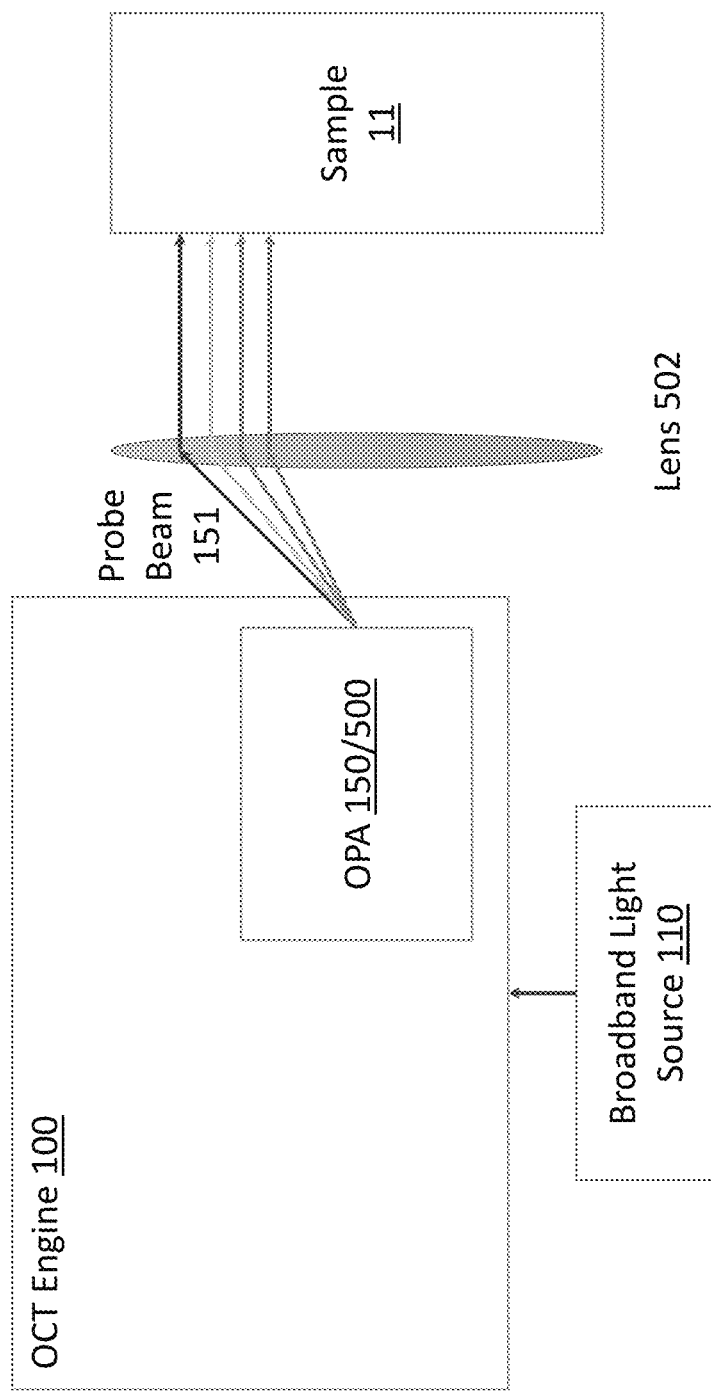
FIG. 5B illustrates dispersion and beam steering by an OCT engine with an OPA.

FIG. 5B illustrates the effect of wavelength-dependent beam steering by the gratings in an OPA 150/500. The OPA 150/500, which is in the focal plane of a transform lens 502, emits the broadband probe beam 151 towards a sample 11.

The grating diffracts the different spectral components of the probe beam 151 at different angles, creating an angular fan or spread that the transform lens 502 turns into a spatial spread on the surface of the sample 11. (For clarity, the different spectral components are represented by discrete arrows in FIG. 5B.)

Tuning the electro-optic phase shifters in the OPA 150/500 steers the beam, and the lens 502 transforms the angular movement of beam by the OPA into translational motion along the sample surface. The spectral dispersion described above causes the different spectral components of the light from the OPA to illuminate different parts of the sample in a deterministic manner as the beam or focused spot sweeps across the sample surface. By measuring the fixed relationship between wavelength and spatial position, the spectral reflectance of the sample at a particular location can be retrieved in post-processing, e.g., by solving a linear inversion representing the OPA dispersion behavior using a regularization method. The tunable wave front shaping capability of an OPA further enables advanced functions such as adaptive focusing, aberration compensation, or systems working in conjunction with eye tracking or motion correction functions.

Figure 6:
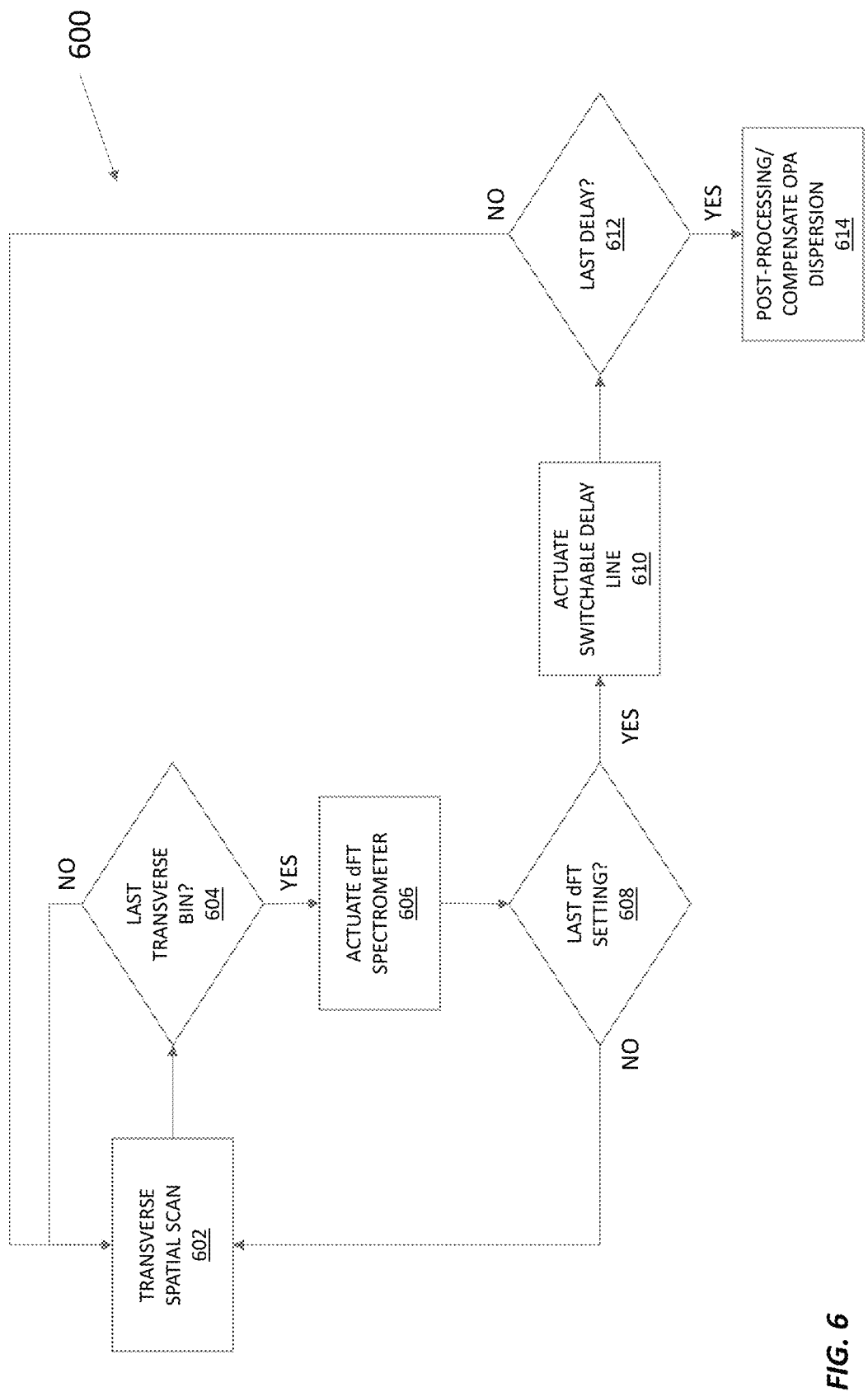
FIG. 6 illustrates a process for acquiring OCT data with a chip-scale OCT optical engine.

FIG. 6 shows a process 600 for acquiring data using a dFT-based OCT engine with an OPA as in FIG. 1A. This process 600 can be executed at video frame rates with little to no sensitivity roll-off with depth over an extended distance. This process 600 differs from conventional OCT acquisition in that it involves conduct one or more transverse spatial scans (B-scans) across the sample with the OPA at MHz or GHz rates with the (thermo-optic) switches in the dFT spectrometer set to a first setting (e.g., the shortest possible path length mismatch) (602). These spatial scans can be performed as rows in a raster scan pattern, a spiral pattern, or a series of spatial modulation patterns, each of which may be different. Once the OPA completes the last scan (604), the switches in the dFT spectrometer are actuated or set to the next path length mismatch (606). These settings can be switched consecutively, e.g., from the shortest path length mismatch to the longest path length mismatch, or non-consecutively, e.g., in leapfrog fashion among different path length mismatches. The OPA then repeats the transverse spatial scan pattern (602) until reaching the last spatial bin (604), at which point the dFT spectrometer is switched to the next setting (606) until reaching the last switch setting for the dFT spectrometer (608).

At this point, the tunable delay line is tuned to the next delay value (610), before the OCT engine scans and switches through the OPA and dFT spectrometer settings, respectively, as described above. The tunable delay line is switched sequentially among several (e.g., 3 to 5) discrete delay values, with each delay value corresponding to a unique imaging depth having zero OPL difference with the reference arm (612). The different delay values re-center the reflection spectrum in its Fourier domain. The OCT engine collects a spectrum at each delay in the tunable delay line, with each spectrum containing undistorted information about the sample profile over a different depth range. The entire depth profile can be extracted from the ensemble of spectra at the different depth ranges/delays.

Once the OCT engine has collected interferograms for every desired combination of dFT setting and reference beam/probe beam delay across the sample, the collected interferograms can be processed to form a volumetric image (C-scan) of the sample (614). This processing may involving compensating for dispersion in the OPA based on the (measured) fixed relationship between wavelength and spatial position of the scanned beam.

CONCLUSION

All parameters, dimensions, materials, and configurations described herein are meant to be exemplary and the actual parameters, dimensions, materials, and/or configurations will depend upon the specific application or applications for which the inventive teachings is/are used. It is to be understood that the foregoing embodiments are presented primarily by way of example and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which at least one example has been provided. The acts performed as part of the method may in some instances be ordered in different ways. Accordingly, in some inventive implementations, respective acts of a given method may be performed in an order different than specifically illustrated, which may include performing some acts simultaneously (even if such acts are shown as sequential acts in illustrative embodiments).

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An optical coherence tomography (OCT) system comprising:
    a light source to emit a broadband beam;
    a beam splitter, in optical communication with the broadband beam, to split the broadband beam into a reference beam and a probe beam;
    a reference arm, in optical communication with the beam splitter, to delay the reference beam;
    a sample arm, in optical communication with the beam splitter, to illuminate a sample with the probe beam and to collect light scattered and/or reflected by the sample in response to the probe beam; and
    a digital Fourier transform (dFT) spectrometer, in optical communication with the reference arm and the sample arm, to measure a spectrum of an interference pattern formed by the reference beam and the light scattered and/or reflected by the sample.

2. The OCT system of claim 1, wherein the beam splitter, the reference arm, the sample arm, and the dFT spectrometer are integrated on a substrate.

3. The OCT system of claim 2, further comprising:
    an optical phased array, integrated on the substrate in optical communication with the sample arm, to steer the probe beam across the sample and to receive the light scattered and/or reflected by the sample in response to the probe beam.

4. The OCT system of claim 1, wherein the reference arm comprises a switchable delay line.

5. The OCT system of claim 4, wherein the switchable delay line comprises:
    an optical switch switchable between a first state and a second state;
    a first waveguide, in optical communication with the optical switch and having a first optical path length, to produce a first time delay when the optical switch is in the first state; and
    a second waveguide, in optical communication with the optical switch and having a second optical path length different than the first optical path length, to produce a second time delay different than the first time delay when the optical switch is in the second state.

6. The OCT system of claim 1, wherein the beam splitter is a first beam splitter and the dFT spectrometer comprises:
    a second beam splitter to split incident light into a first portion and a second portion;
    a first interference arm, in optical communication with the second beam splitter, to receive the first portion of the incident light, the first interference arm comprising:
        a first optical switch switchable between a first state and a second state;
        a reference waveguide, having a first optical path length, to delay the first portion of the incident light by a first delay when the first optical switch is in the first state; and
        a variable waveguide, having a second waveguide length different than the first optical path length different than the first optical path length, to delay the first portion of the incident light by a second delay different than the first delay when the first optical switch is in the second state;
    a second interference arm, in optical communication with the second beam splitter, to receive the second portion of the incident light; and
    a detector, in optical communication with the first interference arm and the second interference arm, to detect interference of the first portion of the incident light from the first interference arm and the second portion of the incident light from the second interference arm.

7. The OCT system of claim 6, wherein the dFT spectrometer further comprises:
    a phase modulator, in optical communication with the second beam splitter, to modulate a relative phase between the first portion and the second portion such that interference of the first portion with the second portion creates a null at a desired wavelength.

8. The OCT system of claim 7, wherein the desired wavelength is a center wavelength of the broadband beam.

9. The OCT system of claim 7, wherein the dFT spectrometer is configured to make a plurality of interferogram measurements between the first portion and the second portion with a null at the desired wavelength in each interferogram measurement in the plurality of interferogram measurements.

10. The OCT system of claim 1, further comprising:
    a waveguide-integrated photodetector, in optical communication with an output of the dFT spectrometer, to detect an output of the dFT spectrometer.

11. The OCT system of claim 10, further comprising:
    an electro-optic modulator, operably coupled to the sample arm, to modulate the probe beam at a reference frequency; and
    a lock-in amplifier, operably coupled to the waveguide-integrated photodetector, to measure a spectral component of the output of the dFT spectrometer whose frequency is locked to the reference frequency.

12. A method of performing optical coherence tomography (OCT) of a sample with a spectrometer with arms comprising cascaded optical switches, the method comprising:
   settings of setting the cascaded optical switches to produce a first path length difference between the arms of the spectrometer, the first path length difference corresponding to a first depth;
   with the cascaded optical switches set to produce the first path length difference:
      scanning a probe beam transversely across the sample;
      collecting light scattered and/or reflected by the sample in response to the probe beam;
      coupling a reference beam and the light scattered and/or reflected by the sample into the spectrometer; and
      detecting interference of the reference beam and the light scattered and/or reflected by the sample at an output of the spectrometers;
   setting the cascaded optical switches to produce a second path length difference between the arms of the spectrometer, the second path length difference corresponding to a second depth different than the first depth;
   with the cascaded optical switches set to produce the second path length difference:
      scanning the probe beam transversely across the sample;
      collecting light scattered and/or reflected by the sample in response to the probe beam;
      coupling the reference beam and the light scattered and/or reflected by the sample into the spectrometer; and
      detecting interference of the reference beam and the light scattered and/or reflected by the sample at an output of the spectrometer; and
   forming a multi-dimensional image of the sample based on the first path length difference, the outputs of the spectrometer with the cascaded optical switches set to the first path length difference, the second path length difference, and the outputs of the spectrometer with the cascaded optical switches set to the second path length difference.

13. The method of claim 12, wherein the spectrometer is integrated on a substrate with an optical phased array and where scanning the probe beam across the sample comprises steering the probe beam with the optical phased array.

14. The method of claim 12, further comprising, before coupling the reference beam into the spectrometer, delaying the reference beam with respect to the probe beam by a first delay with a switchable delay line integrated on a substrate with the spectrometer.

15. The method of claim 14, further comprising, after detecting interference of the reference beam and the light scattered and/or reflected by the sample:
   switching the switchable delay line to delay the reference beam with respect to the probe beam by a second delay different than the first delay; and
   for each of the first path length difference and the second path length difference:
      scanning the probe beam across the sample;
      collecting the light scattered and/or reflected by the sample in response to the probe beam;
      coupling the reference beam and the light scattered and/or reflected by the sample into the spectrometer; and
      detecting interference of the reference beam and the light scattered and/or reflected by the sample at the output of the spectrometer.

16. The method of claim 12, further comprising:
   modulating the probe beam at a reference frequency; and
   measuring a component of the interference of the reference beam and the light scattered and/or reflected by the sample at the reference frequency.

17. The method of claim 12, further comprising:
   forming a volumetric image of the sample based on the interference of the reference beam and the light scattered and/or reflected from the sample.

18. The method of claim 17, wherein scanning the probe beam across the sample comprises angularly dispersing the probe beam and forming the volumetric image comprises compensating angular dispersion of the probe beam.

19. The method of claim 12, wherein scanning the probe beam comprises scanning the probe beam along at least one of a raster-scan pattern, a spiral, concentric circles, or a series of discrete points.

20. The method of claim 12, wherein forming the multi-dimensional image comprises forming an image along a transverse-depthwise slice of the sample.

21. An optical coherence tomography (OCT) system comprising:
   a substrate;
   a beam splitter, integrated on the substrate, to split a broadband beam from a light source into a reference beam and a probe beam;
   a switchable delay line, integrated on the substrate in optical communication with the beam splitter, to delay the reference beam;
   a modulator, integrated on the substrate in optical communication with the beam splitter, to modulate the probe beam at a reference frequency;
   an optical phased array, integrated on the substrate in optical communication with the beam splitter, to illuminate a sample with the probe beam and to collect light scattered and/or reflected by the sample in response to the probe beam;
   a digital Fourier transform (dFT) spectrometer, integrated on the substrate in optical communication with the switchable delay line and the optical phased array, to measure a spectrum of an interference pattern formed by the reference beam and the light scattered and/or reflected by the sample;
   a photodetector, integrated on the substrate in optical communication with the dFT spectrometer, to detect an output of the dFT spectrometer; and
   a lock-in amplifier, operably coupled to the photodetector, to measure a spectral component of the output of the dFT spectrometer whose frequency is locked to the reference frequency.

22. The OCT system of claim 21, wherein the optical phased array comprises at least one electro-optic phase shifter and the dFT spectrometer comprises at least one thermo-optic switch.

* * * * *

UNITED STATES PATENT AND TRADEMARK OFFICE
CERTIFICATE OF CORRECTION

PATENT NO.         : 11,564,565 B2
APPLICATION NO.    : 17/165001
DATED              : January 31, 2023
INVENTOR(S)        : Juejun Hu et al.

It is certified that error appears in the above-identified patent and that said Letters Patent is hereby corrected as shown below:

In the Claims

• In Claim 12, Column 19, Line 7, replace "settings of setting cascaded optical" with -- setting the cascaded optical --

Signed and Sealed this
Fourth Day of July, 2023

Katherine Kelly Vidal
*Director of the United States Patent and Trademark Office*